(12) United States Patent
Gerold et al.

(10) Patent No.: US 7,155,989 B1
(45) Date of Patent: Jan. 2, 2007

(54) TEST PORT

(75) Inventors: Stewart J. Gerold, Greensboro, NC (US); Ronald W. Gardner, Thomasville, NC (US)

(73) Assignee: Environmental Air Systems, Inc., High Point, NC (US)

( * ) Notice: Subject to any disclaimer, the term of this patent is extended or adjusted under 35 U.S.C. 154(b) by 174 days.

(21) Appl. No.: 10/916,192

(22) Filed: Aug. 11, 2004

(51) Int. Cl.
*G01N 1/22* (2006.01)
*G01D 11/00* (2006.01)

(52) U.S. Cl. .................... 73/863.85; 73/866.5

(58) Field of Classification Search ............. 73/863.85, 73/866.5; 374/146, 148, 208
See application file for complete search history.

(56) References Cited

U.S. PATENT DOCUMENTS

| | | | | |
|---|---|---|---|---|
| 490,723 | A * | 1/1893 | Roney | 374/148 |
| 1,609,911 | A * | 12/1926 | Marsh | 374/146 X |
| 3,848,469 | A * | 11/1974 | Chizhov | 73/864.83 |
| 3,918,484 | A * | 11/1975 | Lamb | 137/553 |
| 4,433,587 | A * | 2/1984 | Risdal | 73/863.54 |
| 4,758,688 | A * | 7/1988 | Aschberger | 374/208 X |
| 5,069,072 | A * | 12/1991 | Taylor et al. | 73/866.5 X |
| 5,320,749 | A * | 6/1994 | Mullen | 210/199 |
| 5,483,023 | A * | 1/1996 | Barnes | 174/152 R |
| 5,683,151 | A * | 11/1997 | Friedow et al. | 303/119.2 |
| 5,736,711 | A * | 4/1998 | Joos et al. | 219/132 |
| 6,291,043 | B1 * | 9/2001 | Abbott | 428/36.9 |
| 2003/0110870 | A1 * | 6/2003 | Bigalke | 73/863.85 |

FOREIGN PATENT DOCUMENTS

DE 2237351 A * 2/1974

OTHER PUBLICATIONS

Copy of web page displaying: HVAC Micromanometerl; by Davis inotek Instruments.
Copy of web page displaying: AIRDATA Multimeter ADM-850L; by Shortridge Instruments, Inc.
Copy of web page displaying: Sound Level Meter; two pages includes specifications of same; by Davis inotek Instruments.
Copy of web page displaying: Heated Pentode Refrigerant Leak Detector; by Davis inotek Instruments.
Copy of web page displaying: IAQ-Calc Indoor Air Quality Meter; by Ashtead Technology.
Copy of web page displaying: Temperature and Humidity Meters; by Davis inotek Instruments.
Copy of web page displaying: Combustible Gas Leak Detector; by Davis inotek Instruments.
Copy of web page displaying: Extech Instruments Adjustable Fold-Up Thermometer; by Davis inotek Instruments.

* cited by examiner

*Primary Examiner*—Thomas P. Noland

(57) ABSTRACT

A test port assembly and method are utilized for returning air characteristics within a closed chamber. The test port assembly is positioned in an exterior wall or panel and as required the test port is opened by removing a threaded cap. A thermometer can then be inserted through the test port assembly and the temperature of the air within the chamber quickly determined.

5 Claims, 2 Drawing Sheets

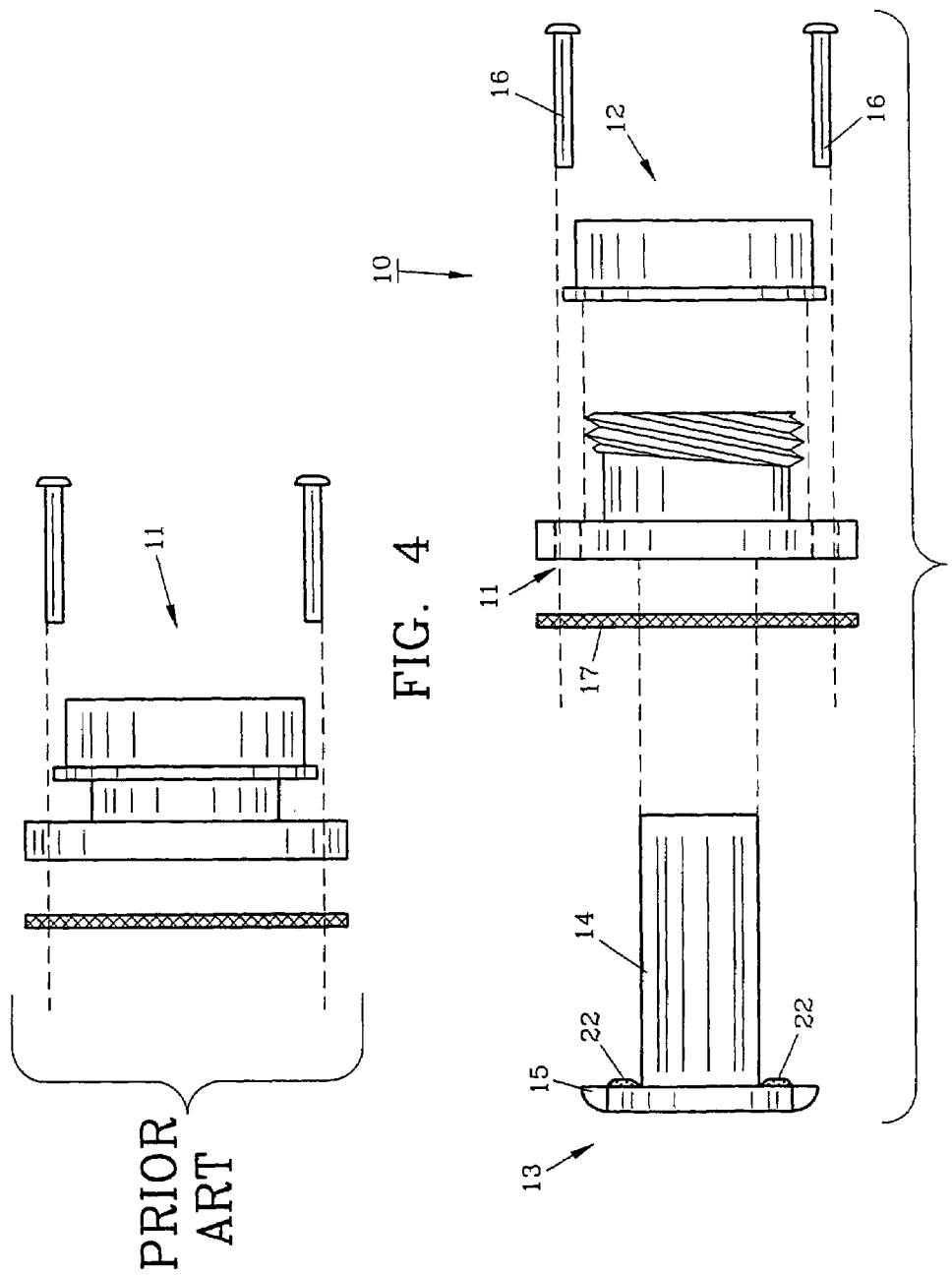

TEST PORT

FIELD OF THE INVENTION

The invention herein pertains to monitoring characteristics of air within a closed chamber and particularly pertains to monitoring the air temperature of a chamber within a building containing air handling equipment.

DESCRIPTION OF THE PRIOR ART AND OBJECTIVES OF THE INVENTION

In recent years maintenance, control and regulation of air handling equipment has become increasingly important as costs to heat, cool and ventilate buildings have escalated. The temperature of the air within such chambers is generally sampled, for example by placing a thermometer through a test port and then reading the temperature to determine the characteristics of the air therein. Other sampling and monitoring instruments may also be employed.

Test ports are affixed to the outer surface of a door, duct or wall panel and provide an opening for the insertion of a thermometer therewithin. However, such test ports are often problematical in that shards of the panel often break free when preparing a channel therein for placement of a test port. Depending on the particular panel construction such shards can either block the channel formed therein or cause damage to or inaccurate readings of the thermometer.

Thus, with the known problems and disadvantages associated with prior art test ports and the ability to take temperature readings therefrom, the present invention was conceived and one of its objectives is to provide a test port assembly which can be quickly and conveniently installed on a door or wall panel.

It is yet another objective of the present invention to provide a test port assembly which includes a flange bushing sized to extend completely through the exterior chamber panel.

It is yet another objective of the present invention to provide a test port assembly having a flanged bushing which is formed from a non-metallic, non-conductive, non-sweating material such as high temperature resistant nylon.

It is a further objective of the present invention to provide a test port assembly which can be quickly adhered to an outside chamber panel using a conventional high temperature resistant caulk.

Various other objectives and advantages of the present invention will become apparent to those skilled in the art as a more detailed description is set forth below.

SUMMARY OF THE INVENTION

The aforesaid and other objectives are realized by providing a test port assembly having an extended bushing with a flange at one end thereof for adhering to the inside surface of a door or wall panel. The bushing is formed from a high temperature resistant polymeric material such as nylon. The bushing is placed through a channel formed in a chambered panel such as a door panel and on the outside surface of the panel a conventional capped test port is affixed.

The method describes use of the test port after installation by removing the cap from the test port, inserting a thermometer through the test port assembly whereupon the temperature of the air within the enclosed chamber can be quickly read. After use the thermometer is withdrawn and the cap replaced on the test port. The preferred method describes the step of drilling a channel through the chamber panel and caulking the bushing flange before its insertion to seal it tightly against the interior surface of the panel.

BRIEF DESCRIPTION OF THE DRAWINGS

FIG. 1 demonstrates in exploded fashion the test port assembly of the invention;

FIG. 4 shows a view of an old test port.

DETAILED DESCRIPTION OF THE PREFERRED EMBODIMENT AND OPERATION OF THE INVENTION

Figure 3:
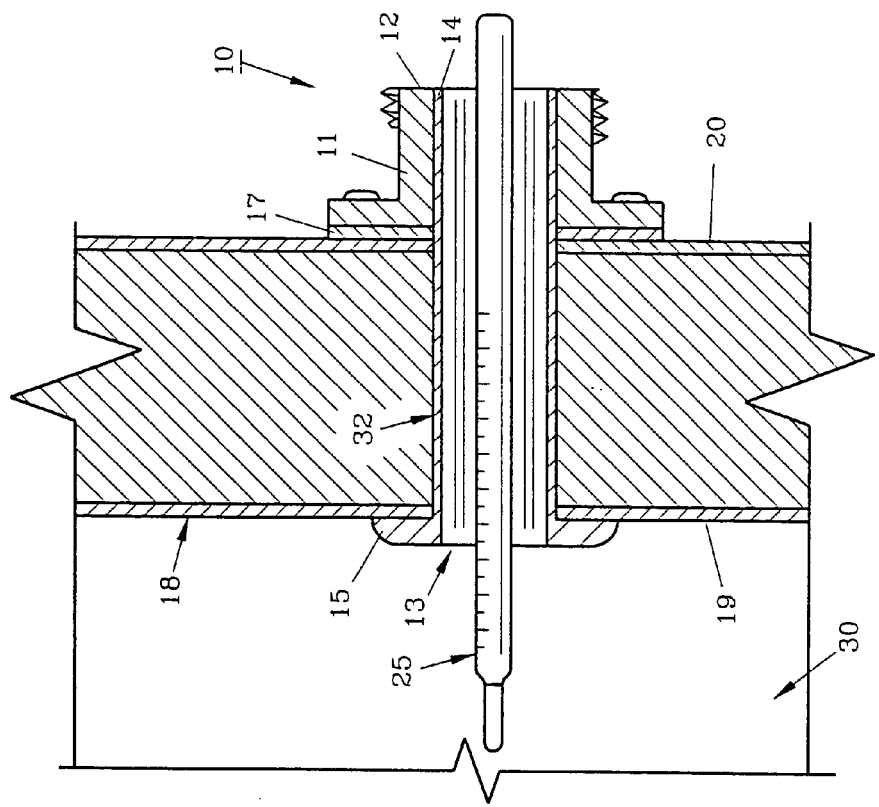
FIG. 3 demonstrates in a cross-sectional view the use of the test port assembly with the cap removed and a thermometer positioned therethrough.

For a better understanding of the invention and its operation, turning now to the drawings, FIG. 1 shows an exploded view of the test port assembly of the invention as removed from a wall. As illustrated by test port assembly 10 which includes test port 11, cap 12 and elongated bushing 13. Bushing 13 is preferably formed from a non-metallic, non-conductive, non-sweating material such as a high temperature resistant nylon as is conventionally available and includes tube 14 integrally formed with flange 15. Tube 14 extends for example two and one-half inches (2½" or 6.35 cm) and has an inside diameter of three-quarters of an inch (¾" or 1.9 cm). The length of bushing 13 is adequate for placement of test port assembly 10 on a two inch (2") thick door or wall panel.

Figure 2:
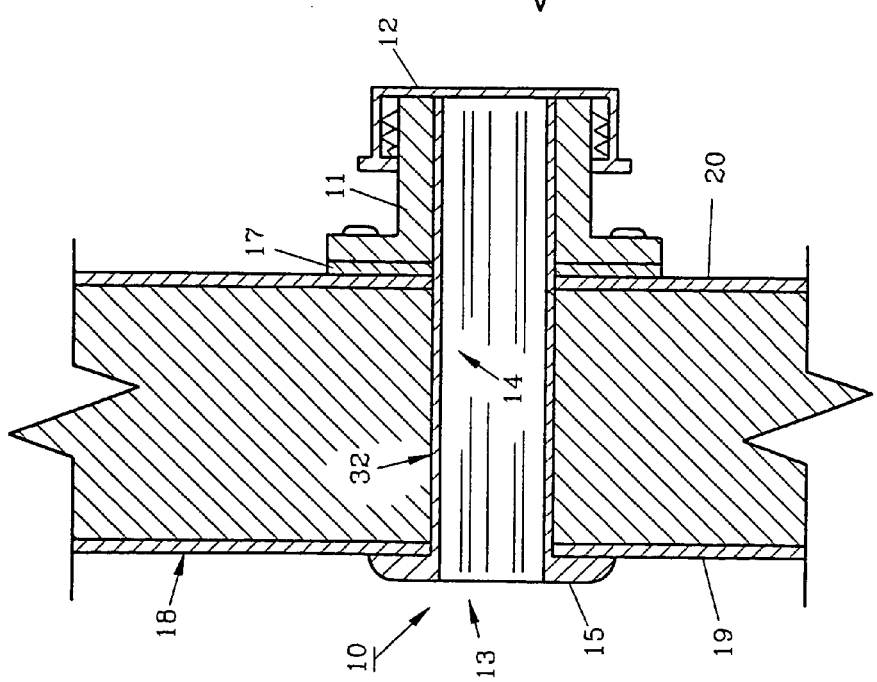
FIG. 2 shows the test port assembly in cross-sectional view enclosed in a typical door panel.

In FIG. 2, test port assembly 10 is shown mounted in a typical two inch (2" or 5.0 cm) polyurethane insulated door panel which is used as an entryway into an air handling equipment chamber such as inside a building. Door panel 18 shown in FIG. 2 includes an interior panel surface 19 and an outside or exterior panel surface 20. While the examples herein demonstrate the typical assembly affixed to a chamber door panel such a test port assembly could likewise be used on other structures such as air ducts, walls, ceilings and the like.

In FIGS. 2 and 3, flange 15 is shown abutting into panel surface 19 and is adhesively joined thereto with conventional high temperature resistant silicon caulk 22 (FIG. 1). Caulk 22 seals flange 15 to interior panel surface 19 of door panel 18. Tube 14 extends from flange 15 through door panel 18 and into test port 11 as shown in FIGS. 2 and 3. Thus, bushing 13 forms a passageway completely through door panel 18 and test port 11. Thermometer 25 is shown in FIG. 3 passing through bushing 13 for sampling the air within chamber 30.

The preferred method of the invention comprises forming a hole through an exterior chamber wall or panel such as by drilling channel 32 through panel 18 as shown in FIGS. 2 and 3 using an electric drill or other conventional tool. With channel 32 so formed, tube 14 of elongated bushing 13 is then placed therein, caulking 22 is applied to the inside edge of flange 15. Tube 14 is then pushed completely through channel 32 with flange 15 abutting interior panel surface 19 as seen in FIGS. 2 and 3 and sealed thereto by caulk 22. Next, conventional test port 11 as seen in FIG. 4 is placed over the protruding end of bushing tube 14 and is affixed to exterior panel surface 20 of door panel 18 with flexible gasket 17 therebetween. Conventional rivets 16 rigidly affix test port 11 to door panel 18. Cap 12 is then threadably placed thereon.

As required, cap 12 can be removed from test port 11 and the temperature of chamber 30 shown in FIG. 3 can be easily taken by inserting thermometer 25 through test port assembly 10. Bushing 13 provides for secure and convenient placement of thermometer 25 without concern for damage by shards from channel 32 of door panel 18 which may also restrict or hinder placement of thermometer 25 therein. After the temperature of the air within chamber 30 is taken, thermometer 25 is removed and cap 12 is threadably replaced on test port 11.

The illustrations and examples provided herein are for explanatory purposes and are not intended to limit the scope of the appended claims.

We claim:

1. A test port assembly comprising: a test port, a bushing, said bushing comprising a tube, a flange, said flange affixed to said tube, said bushing formed from a high temperature resistant polymeric material, a cap, said cap releasably affixed to said test port, a high temperature resistant caulk, said caulk affixed to said flange, said tube extending through said test port, said bushing extending from said test port and in fluid communication therewith.

2. The assembly of claim 1 wherein said polymeric material comprises a non-conducting nylon.

3. A test port assembly for air sampling inside a closed chamber having walls comprising: a test port, said test port positioned on the outside of one of the chamber walls, a cap, said cap releasably positioned on said test port, a bushing, said bushing comprising a tube, a flange, said flange affixed to said bushing, said bushing positioned through the inside of the chamber wall and extending through said test port to said cap where said cap is affixed to said test port in fluid communication therewith.

4. The assembly of claim 3 further comprises caulk, said caulk positioned on said flange, and a gasket, said gasket placed between the wall and said test port.

5. The assembly of claim 3 wherein said bushing is formed from a non-conducting nylon.

* * * * *